United States Patent [19]
Wade

[11] Patent Number: 5,490,781
[45] Date of Patent: Feb. 13, 1996

[54] ADJUSTABLE, SANITARY, NON-REUSABLE HIGH SPEED AND LOW SPEED DENTAL HAND PIECE GLOVE (COVER) AND NOISE REDUCER

[76] Inventor: Eric V. Wade, P.O. Box 8345, Tyler, Tex. 75711

[21] Appl. No.: 942,729

[22] Filed: Sep. 9, 1992

[51] Int. Cl.$^6$ ..................... A61C 1/16
[52] U.S. Cl. ..................... 433/116
[58] Field of Search ..................... 433/115, 116

[56] References Cited

U.S. PATENT DOCUMENTS

| | | | |
|---|---|---|---|
| 1,485,963 | 3/1924 | Curry | 433/116 |
| 4,266,935 | 5/1981 | Hoppe | 433/116 |
| 4,286,950 | 9/1981 | Hawk | 433/116 |
| 4,693,871 | 9/1987 | Geller | 433/116 |
| 4,728,290 | 3/1988 | Eisner et al. | 433/116 |
| 4,752,223 | 6/1988 | Carlson | 433/116 |
| 4,789,336 | 12/1988 | Lewis | 433/116 |

FOREIGN PATENT DOCUMENTS

| | | | |
|---|---|---|---|
| 3627144 | 3/1987 | Germany | 433/116 |
| 8802215 | 4/1990 | Netherlands | 433/116 |

*Primary Examiner*—Nicholas D. Lucchesi
*Attorney, Agent, or Firm*—Odesa Gorman Stapleton

[57] ABSTRACT

An adjustable, sanitary, disposable improved dental hand piece cover and dental hand piece noise reducer, having an adjustable head section (28), an adjustable neck section (36), and cylindrical body and handle section, with internally stabilizing and noise reducing material (34), by the utilization of which the dental hand piece is prevented from coming in direct contact with the patients oral cavity or its possible harmful inclusions. The cover is formed of a plastic material, preferably by the process of injection molding or thermoforming of a predetermined shape corresponding to that of the general conventional hand piece to be used. The cover comprises an assembly of two individual halves of injection molded or thermoformed material, that when forcibly united will amply and completely encase the dental hand piece. At least one model variation is formed for use specifically with a slow-speed dental hand piece. When desired to be used, the hand piece cover is removed from its pre-packaging and the dental hand piece is centered and then laterally inserted into either half of the hand piece cover (116) or (120). If a fiber optic light is used, the model of the hand piece cover which includes fiber optic light cover (56) may be used. Any variations in head width or contra-angle position may be compensated for by the flexing and adjustable sections of the head (28) and neck (36) regions. The connecting sections (32 and 32') are then aligned and forcibly united until the two halves interlock, thus forming the hand piece cover assembly with the dental hand piece being internally stabilized by material (34). After use, the hand piece cover (116) or (120) may be removed and then properly disposed of.

14 Claims, 4 Drawing Sheets

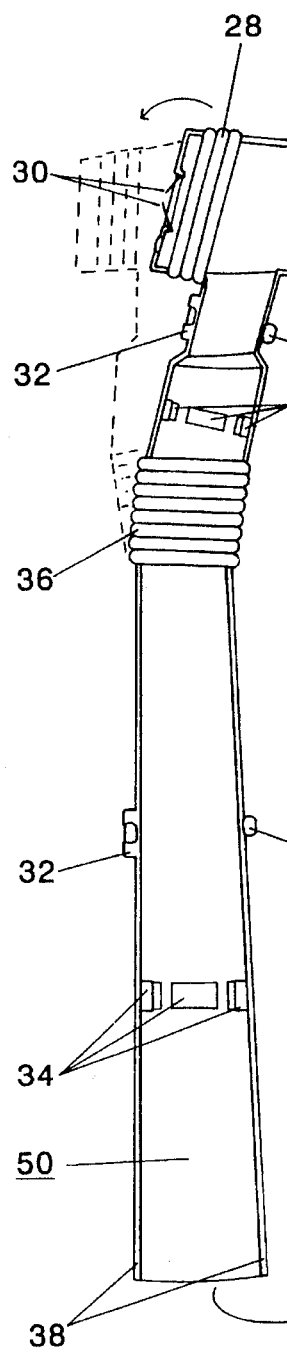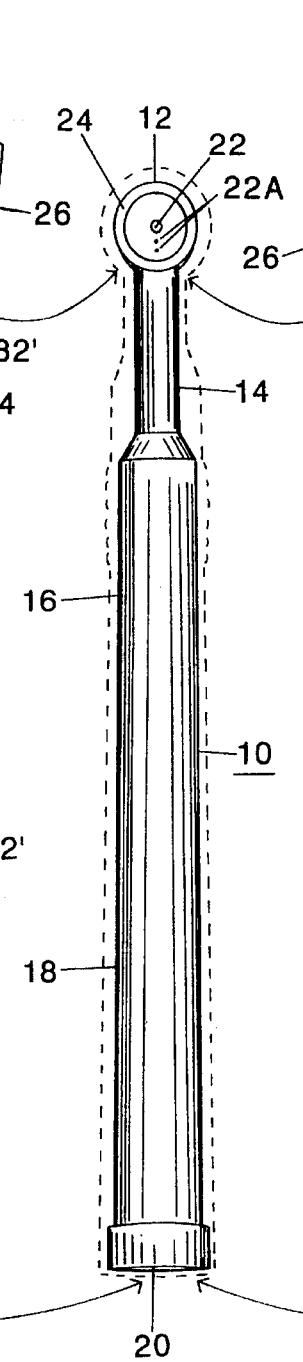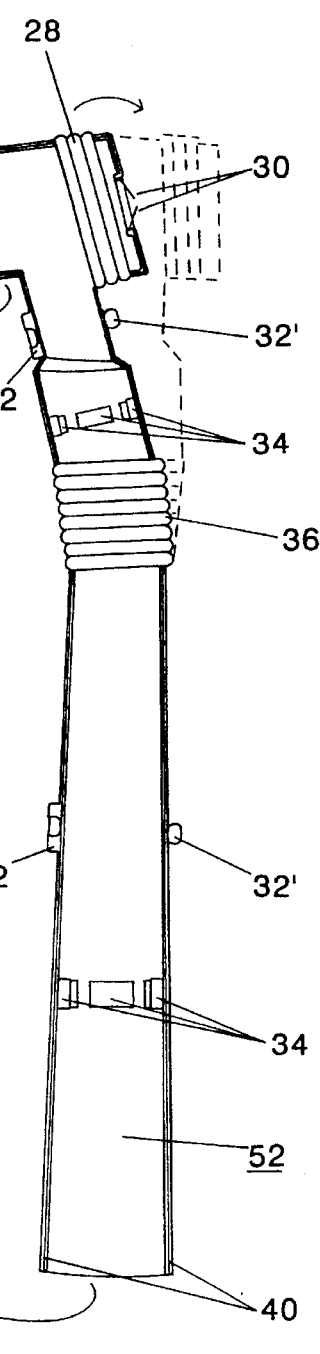
Fig. 1A   Fig. 1B   Fig. 1C
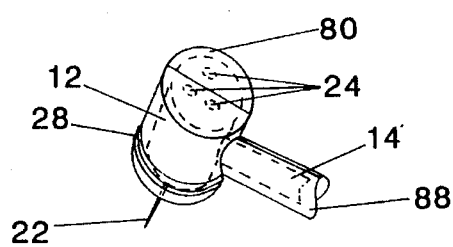
Fig. 2

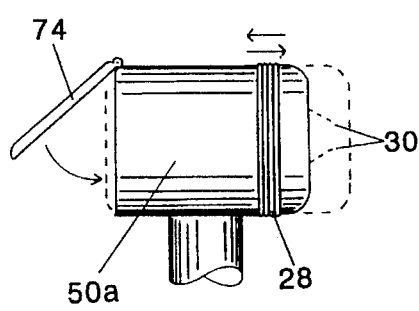
Fig. 8B
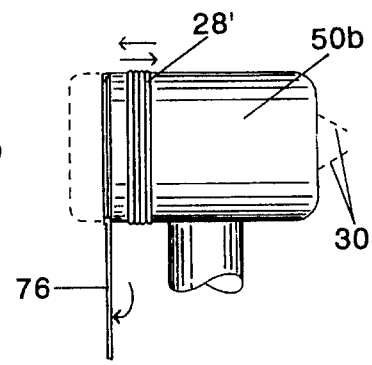
Fig. 8C
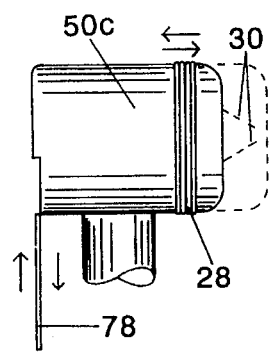
Fig. 8D
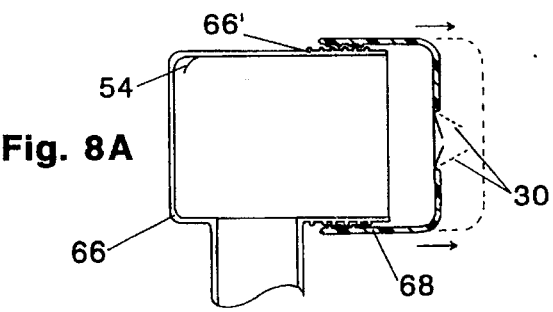
Fig. 8A
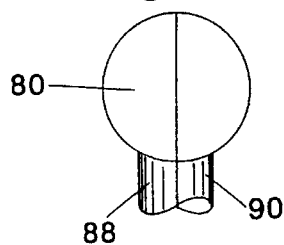
Fig. 7B
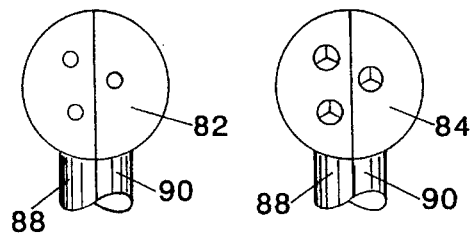
Fig. 7C
Fig. 7D
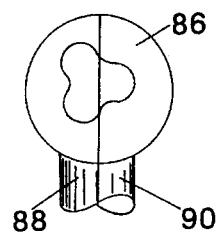
Fig. 7E
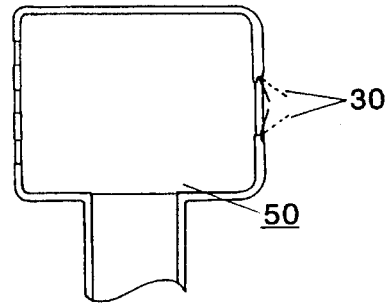
Fig. 7A

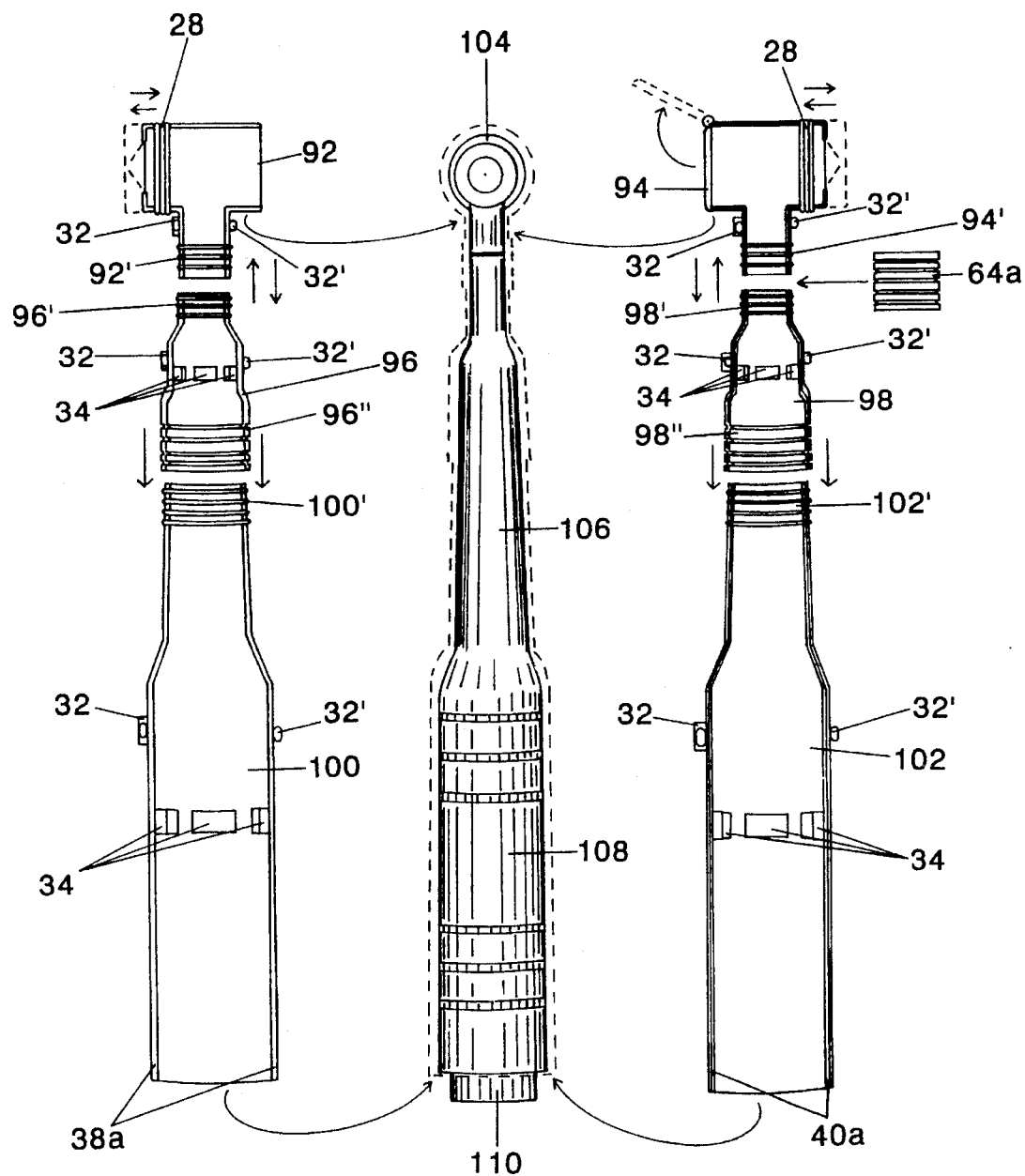

ADJUSTABLE, SANITARY, NON-REUSABLE HIGH SPEED AND LOW SPEED DENTAL HAND PIECE GLOVE (COVER) AND NOISE REDUCER

BACKGROUND—FIELD OF INVENTION

This invention relates primarily to the practice of Dentistry and more specifically to an apparatus to be used for the purpose of reducing harmful (potentially ear damaging) dental hand piece noises to the dentist and patient, as well as to prevent the dental hand piece from becoming a source of transmitting any disease found within the oral cavity or any other blood borne pathogen.

BACKGROUND—DESCRIPTION OF PRIOR ART

In recent years the various health professions have come under close scrutiny due to the increase in number of life threatening infectious diseases and the threat of their transmission from doctor to patient, patient to doctor, and of course patient to patient. As a result of this increased concern, OSHA (the Occupational Safety and Health Administration) has issued specific guidelines for the various health professions dealing with these new and increasingly vital national concerns.

Many efforts have been made and new products introduced that have been aimed at preventing the dental office setting from becoming a source of disease transmission. Such items as disposable cleaning devices (prophyangles), oral evacuation tips, protective eye wear, and latex gloves have all proven to very useful in helping to reduce direct contact of the patients oral cavity with a re-usable appliance. With the continued use of these and other disposable items it can be logically assumed that the incidence of accidental exposure to potentially dangerous microorganisms will be reduced.

As successful as these and other attempts have been, there still remains a possible if not proven source of pathogen transmission within the dental office, that being the air-driven dental hand piece. With the predicted increase in the numbers of cases of Hepatitis B and the HIV virus, dentists will be treating more of these patients in all stages of the disease. With a greater number of patients seen in the dental office setting, comes a greater possibility of accidental exposure to infectious diseases.

Because of these vital health concerns, OSHA has issued detailed guidelines for proper handling and sterilization of dental hand pieces following each patient use. Proper hand piece sterilization involves autoclaving the instrument at approximately 15 psi (pounds per square inch of pressure) at a temperature of 121 degrees Centigrade for a period of 30 minutes.

Routine dental procedures involve the use of both the high speed and low speed air driven dental hand pieces. Due to the fact that the hand piece comes into direct contact with the patients oral cavity during use, it becomes a very vital link in the chain of infection transmission in addition to being an item of patient concern. During routine use, the dental hand piece is found to collect blood, minute debris and other microbial and particulate matter. These "collections" have proven to be a source of blood borne pathogen transmission including those responsible for Hepatitis B and the HIV virus.

It has been proven the commonly used, time saving method of chemical disinfecting and cold (chemical) sterilization after use is not sufficient to kill 100 percent of the potentially harmful saliva and blood borne pathogens that may be found in the dental patient pool.

It is now a requirement that each dental hand piece be autoclaved after each use. This requirement, though necessary, will drastically reduce the number of patients effectively treated during the normal day due to the increased time requirement to both autoclave and cool the instruments. The cost of the dental hand pieces range from a couple of hundred dollars to over a thousand (with accessories included). This fact makes it a difficult if not economically impossible task to provide each patient with the safety and mental peace of mind of having their own private hand piece. There is then an apparent immediate need for a device that is adjustable enough in nature to be used with a variety of available dental hand pieces (both high and low speed). It has been shown that the autoclave process may over a period of time actually damage the internal workings of the hand piece. Such repetitive autoclaving is also shown to in time decrease both the speed and efficiency of normal hand piece operation, resulting in decreased life of the instrument.

To summarize this problem, there exists at present no universally useful and practical method of preventing the dental hand piece (either high speed or low speed) from coming in direct contact with potentially harmful fluids or blood borne pathogens found within the oral cavity.

Another, perhaps less publicized concern which relates to the routine practice of dentistry is the issue of occupational noise and hearing loss. The high speed dental hand piece is shown to produce noises in the frequency range of 2000 Hz to 3500 Hz (with other older instruments probably higher).

The Journal of the American Medical Association has recently published an article stating that "in the United States, about 28 million people have hearing loss, and exposure to loud noises is at least partially responsible for the hearing impairment of 10 million of these persons." The issue of industrial noise and its relationship to NIHL (Noise Induced Hearing Loss) is one important enough to be regulated by guide lines from OSHA and NIOSH (National Institute of Occupational Safety and Health). Current findings show that permanent hearing loss may be experienced by exposure to noises of 85 decibels or more for prolonged periods of time. The dental hand piece produces at the frequency of 2000 Hz a noise of 80 decibels, which over a period of time can lead to the dentist experiencing impaired hearing. With the average dentist spending hours per week (for any number of years) at the chair-side while operating the unprotected hand piece, the potential readily exists for the practitioner to experience some type of hearing disorder. This is in fact the case for a small number of practitioners (at the present time) though it is difficult to determine exactly how much abuse the ear can withstand before malfunctioning it has been shown that noise in excess of 90 db (decibels) for eight hours over 92 dB for only six hours may well act to weaken the ear making it more susceptible to future insult. The Occupational Safety and Health Administration has provided what they consider to be "safe limits" of noise exposure with maximum allowable time of exposure at actual decibel levels. They are: eight hours at 90 dB, six hours at 92 dB, four hours at 95 dB, two hours at 100 dB, one hour at 105 dB, thirty minutes at 110 dB, fifteen minutes or less at 115 dB, 120 dB considered to be loud enough to produce a hearing loss. For a better understanding of the decibel as used in measurement of sound intensity; the rustling of leaves is about 20 dB, while a soft whisper at five feet is approximately 25 dB. A typical dental hand piece at 2000 Hz frequency is 80 dB, while a jackhammer is 90–110 dB.

Most common soft silicone ear plugs will attenuate sound approximately 15 to 35 decibels depending on the frequency of the stimulus. Ear muffs or "ear defenders" can often reduce noise levels by 40 to 45 decibels.

At present, there is no device on the market that performs the functions of this invention, although the profession is in much need of one. U.S. Pat. No. 4,693,871 to Geller (Sep. 15, 1987) proposes a "Disposable Aseptic Sheath for Dental Hand Pieces". U.S. Pat. No. 4,728,290 to Eisner (1987) proposes a "Dental Hand Piece Shield Or Prophylactic" and U.S. Pat. No. 4,789,336 to Lewis (1987) proposes an "Art of Protecting A Dental Instrument". Each of these devices make several claims the practical disadvantages of which will be addressed in the paragraphs to follow.

(a) Each of the above devices claim to be removable, and are so. Their removal however would prove to be cumbersome and time consuming during a routine dental procedure. During the course of routine dental procedures the dental bur will often need changing in order to obtain a desired preparation, the "rubber like, elastic, pliable material" to be used in U.S. Pat. No. 4,789,336 to Lewis (1987) would require complete stoppage, then an "unrolling" of the sleeve (which during normal operating conditions would be wet with water spray as well as saliva) after which an attempt would be made to replace the device without contamination of the hand piece by allowing it to come into direct contact with the outer portion of the sleeve.

A similar situation would hold true for the device which is the subject of U.S. Pat. No. 4,728,290 to Eisner (1987). U.S. Pat. No. 4,693,871 to Geller (1987) has a wrap around arrangement, which would prove to be difficult since it is to be vacuum formed. Such vacuum forming will give the end result of a cover which will conform exactly to the dimensions of the item vacuum formed. This procedure performed under normal vacuum forming procedures would leave no overlapping material. The overlapping region would then have to be physically added to this exact external replica of the instrument in order for an overlapping "seal" to take place.

(b) Neither of the three above mentioned U.S. Patents addresses a method of stabilizing the hand piece while inside the covering. It is possible and very likely that a pliable, rubber like covering such as the one mentioned in U.S. Pat. No. 4,789,336 to Lewis (1987) would twist and deform around the hand piece if for example any unexpected forces (such as a child biting down suddenly) were introduced. In this or a similar situation, the possibility of tearing or rupture of the sleeve would also be of concern. As a result, slippage or sudden change in tactile feel may be experienced during operation. The device mentioned in U.S. Pat. No. 4,693,871 to Geller (1987) also makes possible the turning of the hand piece during use while inside the sheath. The overlapping of the plastic alone without any internal bracing or stabilization would in most cases not be sufficient to prevent the movement of the instrument. Without this or some other means of internally securing or stabilization of the hand piece, instruments of varying width and circumference would not be adequately secured while the hand piece was in operation.

(c) While U.S. Pat. No. 4,693,871 to Geller (1987) make the claim to totally enclose the hand piece, as does U.S. Pat. No. 4,728,290 to Eisner (1987), the head regions of each device possess openings that allow for the changing of the bur. These openings will allow direct contact of the hand piece with any oral fluids and therefore possible contaminants therein. This may occur if and when saliva, other fluids as well as microscopic viral and bacterial matter enter the spaces between the sheath and the hand piece itself.

(d) In the patents mentioned above, no attention is given to the front region of the head portion of the devices through which the bur passes. This unchallenged opening is another possible source of oral fluid contact and therefore a site of possible exposure to undesirable debris and or pathogens.

(e) The rear openings of the patents mentioned above also allow for the escape of air from the rear of the dental hand piece during normal use. This concentrated air (usually between 20–40 pounds per square inch) while necessary to drive the air driven hand piece also acts as a propellant for water, blood, saliva, any blood borne pathogens or other potentially harmful matter found in the setting. This mist which is often clearly visible, may itself be a source of disease transmission, especially to any air borne pathogen.

(f) Neither of the patents mentioned above have a provision for the fiber optic light portion of the hand piece commonly used by many practitioners.

(g) Neither of the patents mentioned above have a provision for adjusting or flexing of the head region of the device. Such flexibility in either the forward or backward direction will allow for the fitting of a wide variety of varied angled hand pieces currently on the market.

(h) It has not been found in either of the aforementioned patents a provision for reducing the potentially harmful noises produced by the air-driven hand piece during normal use.

(i) U.S. Pat. No. 4,693,871 to Geller (1987) proposes an overlapping wrap around method of closing. In the normal dental operating field this method of closure may be compromised by a patient biting down and by doing so exert enough pressure to distort the wrap thereby causing leakage of saliva, water, blood borne pathogens and other particulate matter into the device.

(j) U.S. Pat. No. 4,693,871 to Geller (1987) is to be manufactured by the process of vacuum forming. This process would make it very difficult as well as expensive for use on a wide scale basis due to the large number and many variations of the hand pieces available today.

(k) A commonly recognized fear of the dental profession is the dental handpiece. Its appearance alone is an anxiety producing factor for some patients both young and old. No provision exists in either of the above mentioned patents that addresses this problem as it relates to the dental hand piece.

OBJECTS AND ADVANTAGES

Accordingly, besides the objects and advantages of the various features described in the subject of this patent application, several other objects and advantages of this invention are:

(a) to provide a method of closure (friction locked hinges) which will better secure the hand piece inside the device.

(b) to provide a more secure barrier to leakage by the use of the extended strip-groove interlock of the device.

(c) to provide for a more complete seal on the rear portion of the head region of the cover by the use of either a device with no rear cap, or by the use of one of the mentioned friction lock caps.

(d) to provide for the reduction of harmful noise produced by the dental hand piece by the use of internally placed rubber or sponge-like foam or by the total encasement of the hand piece.

(e) to provide for non-slippage of the hand piece by the use of internal rubber strips or sponge-like material.

(f) to provide for use of a variety of available hand pieces by the features of the "bellowed plastic" at the base of the head region and the adjustable "bellowed plastic" band in the head region itself.

(g) to provide an adjustable, sanitary, disposable hand piece cover and noise reducer for use with a wide variety of conventional slow-speed dental hand pieces.

(h) to provide for the reduction of "exhaust" from the air driven dental hand piece by enclosing the rear portion of the head of the device.

(i) to provide for the reduction in patient apprehension by the use of opaque colors, color combinations, designs, characters and or any combination thereof.

(j) to provide an increased barrier to prevent entry of unwanted substances in the front of the dental hand piece by the use of the "pie-shaped" cover situated over the area of the hand piece through which the bur protrudes.

(k) to provide a device which will more efficiently prevent the spread of infectious disease or blood borne pathogens.

(l) to provide the practitioner with a device that will allow easy access to the rear of the hand piece without exposing the instrument to contamination.

(m) to provide the practitioner with a device that allows for more ease of handling during operation (while wearing latex or vinyl gloves) by the use of varied textured surfaces and or designs.

(n) to provide the practitioner with a device which allows for the unobstructed use of the fiber optic light during the procedure by using a clear plastic covering in the respective area of the hand piece.

(o) to provide the practitioner with a device which will actually magnify the amount of light produced by conventional fiber optic light sources by incorporating a "magnifying" piece of plastic over the region of the fiber optic light opening.

Further objects and advantages are to provide the profession with a new and improved method of preventing the dental hand piece from becoming a source of disease transmission, which may be mass produced and thereby made practically available to all practitioners. Such mass production will be obtained by using the aforementioned precision designed, "pre-formed mold" method. This method should serve to drastically reduce manufacturing cost over previously prescribed methods and as a result produce a product which will be readily affordable for the private practitioner, clinic or school/research setting.

The primary objects and advantages of this invention are:

1) To provide the patient, dentist/practitioner and auxiliary personnel with a new and more effective means of preventing the transmission of infectious diseases or blood borne pathogens via the high speed air driven dental hand piece (instrument).

2) To provide the patient, dentist/practitioner and auxiliary personnel with a new and improved mechanism for preventing the transmission of infectious diseases or blood borne pathogens via the slow-speed air driven dental hand piece.

3) To provide the patient, dentist/practitioner and auxiliary personnel with a device which will reduce the harmful, potentially ear damaging noises produced by the air driven dental hand piece, and thereby helping to prevent noise induced hearing loss in the workplace.

4) To provide a conveniently used dental hand piece covering that is easy to manipulate, while at the same time adjustable in nature so that a wide variety of available (and future available) hand pieces may be utilized.

5) To provide a device which will help alleviate and or reduce patient anxiety directed towards the hand piece, as well as to increase patient confidence and peace of mind as it relates to their safety and well being while undergoing dental treatment.

DRAWING FIGURES

In the drawings, closely related figures have the same number but will have different alphabetic suffixes attached.

Brief Summary of Figures

FIGS. 1A–1C are is intended to show a front view of a typical high speed air driven dental hand piece with which the adjustable, disposable dental hand piece cover and noise reducer (the invention) can be used accordingly, illustrating the relative position of the hand piece as it is to be contained within the two halves of the invention:

FIG. 2 is intended to show a perspective view of one embodiment of the sanitary cover in accordance with the adjustable, disposable dental hand piece cover and noise reducer as it is to be used with the typical high speed hand piece shown in FIG. 1.

FIGS. 7A–7E intended to show a rear view of the variations of one embodiment of the back portion of the head section of the dental hand piece cover in accordance with the invention.

FIGS. 8A–8D are intended to show a side view of the variations of the adjustable component of the head section of the dental hand piece cover in accordance with the invention, as well as to illustrate the direction of its range of motion or flexibility and will also show the variations or types of rear "caps" or "covers" present in one embodiment of the back portion of the head section of the dental hand piece cover (found in FIG. 7) in accordance with the invention:

FIGS. 10A–10C are intended to show a side view of one embodiment of the adjustable, disposable, dental hand piece cover in accordance with the invention as it is to be used with the typical low speed dental hand piece.

Figure 3:
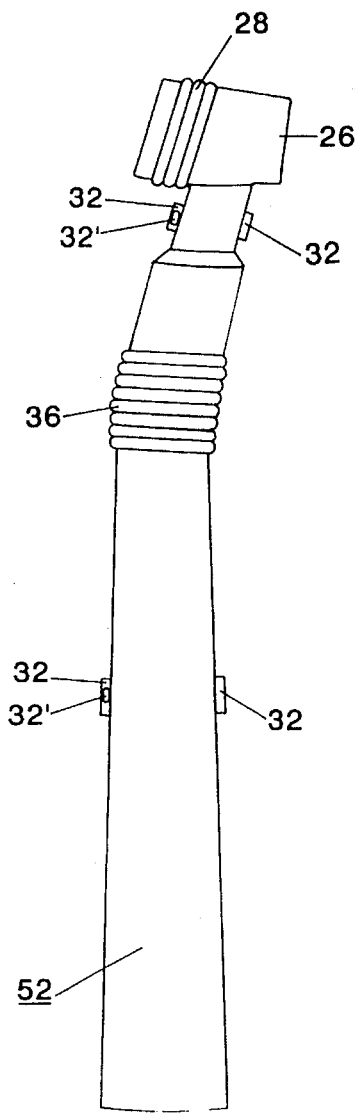
FIG. 3 is intended to show a left side, external view of the dental hand hand piece cover.

| Reference Numerals In Drawings | |
|---|---|
| 10 | High Speed (Air Driven) Dental Hand piece |
| 12 | Head Portion of Hand Piece-10 |
| 14 | Neck Portion of Hand Piece-10 |
| 16 | Body Region of Hand Piece-10 |
| 18 | Handle Region of Hand Piece |
| 20 | Bottom Opening of Hand Piece |
| 22 | Dental Bur |
| 22a | Air-Water Opening |
| 24 | Rear Openings of Hand Piece (for Bur Changing) |
| 26 | Closed Rear Region of Head Section of Cover |
| 28 | Adjustable Feature of Head Section—Front Positioned |
| 28' | Adjustable Feature of Head Section—Rear Positioned |
| 30 | Front Bur Opening Cover |
| 32 | Female Portion of Friction Interlocking Hinge Device |
| 32' | Male Portion of Friction Interlocking Hinge Device |
| 34 | Noise Absorbing, Dental Hand Piece Stabilizing Sponge/Foam Material |
| 36 | Adjustable "Bellowed Plastic" Feature of the Neck Section |
| 38 | Receiving Groove of Closing Overlap Seal with High-Speed Model |
| 38a | Receiving Groove of Closing Overlap Seal with Slow-Speed Model |
| 40 | Interlocking Extension of Closing Overlap Seal with High-Speed Model |
| 40a | Interlocking Extension of Closing Overlap Seal with Slow-Speed Model |
| 50 | (Entire) Right Half of Dental Hand Piece Cover: High-Speed Model |
| 50a | Head Section of Hand Piece Glove with Flip-Top Rear Cover (74) |
| 50b | Head Section of Hand Piece Cover with Swivel-Motion Rear cover |
| 50c | Head Section of Hand Piece Cover with Sliding-Lock Motion Rear Cover |
| 52 | (Entire) Left Half of Dental Hand Piece Cover: High-Speed Model |
| 54 | Air Defector |
| 56 | Cover for Fiber Optic Light of Hand Piece |
| 60 | Top Left Section on Dental Hand Piece Cover with Model Utilizing Collar Connector |
| 62 | Bottom Section of Dental Hand Piece Cover with Model Utilizing Collar Connector |
| 64 | Adjustable Collar Connector |
| 64a | Adjustable Collar Connector for Slow-Speed Model |
| 66 | Head Section (Enclosed) To Be Used with 68 |
| 66' | Graded Notched Friction Lock Portion of 66 |
| 68 | Snap-On Cover (used with 66) |
| 70 | Top Right Section of Hand Piece Cover Utilizing Collar Connector |
| 72 | Bottom Right Section of Hand Piece Cover Utilizing Collar |
| 74 | Flip-Open Rear Cover |
| 76 | Swivel Motion Rear Cover |
| 78 | Sliding Motion Rear Cover |
| 80 | Fully Enclosed Rear Cover |
| 82 | Head Section with Covered |
| 84 | Head Section with Rubber or Plastic Covered (Bur Tool) Openings |
| 86 | Head Section with Continuous Single Covered Opening |
| 88 | Left Half of High-Speed Dental Hand Piece Cover |
| 90 | Right Half of High-Speed Dental Hand Piece Cover |
| 92 | Head Section of Hand Piece Cover Utilizing Collar Connector/Right Half |
| 92' | Grooved Connecting Portion of Right Half |
| 94 | Top Section of Hand Piece Cover for Slow-Speed Hand Pieces Utilizing Flip-Open Rear Cover |
| 94' | Grooved Connecting Portion of 94 |
| 96 | Center Connection Collar for Slow-Speed Cover-Right Half |
| 96' | Top Grooved Connecting Portion of Center Connecting Collar/Right Half |
| 96" | Bottom Grooved Connecting Portion of Collar/Right Half |
| 98 | Center Connection Collar for Slow-Speed Hand piece Cover |
| 98' | Top Grooved Connecting Portion of Collar/Left Half |
| 98" | Bottom Grooved Connecting Portion of Collar/Left Half |
| 100 | Bottom Section of Slow-Speed Hand Piece Cover/Right Half |
| 100' | Grooved Connecting Portion of Bottom Section/Right Half |
| 102 | Bottom Section of Slow-Speed Hand Piece Cover/Left Half |
| 102' | Grooved Connecting Portion of Bottom Section/Left Half |
| 104 | Head Region of Conventional Slow-Speed Air Driven Dental Hand Piece |
| 106 | Neck/Body Section of Slow-Speed Dental Hand Piece |
| 108 | Handle Region of Slow-Speed (Conventional) Hand Piece |
| 110 | Bottom Opening of Conventional Slow-Speed Dental Hand Piece |
| 112 | Raised Surface Texture: Dot (Stippling) Design |
| 114 | Raised Surface Texture: Line Pattern Design |
| 116 | Adjustable, Disposable, Sanitary Dental Hand piece Cover (High Speed model) |
| 118 | Conventional Slow-Speed Dental Hand piece |
| 120 | Adjustable, Disposable, Sanitary Dental Hand piece Cover (Low-Speed Model) |

DESCRIPTION OF FIGS. 1 TO 10

Referring now to the drawings wherein like reference characters shall designate identical or corresponding parts throughout the various views. A typical conventional high-speed air-driven dental hand piece (designated in FIG. 1B) with which the hand piece cover in accordance with the cover (116) is used is shown in FIGS. 1A and 1C. A typical embodiment of the opened position of the present invention is illustrated in FIG. 1A (an internal side view of the right half of the invention) and FIG. 1B (internal side view of the left half of the invention). The typical high-speed air driven dental hand piece 10 consists of a head region 12 connected to one end of a neck region 14 and then to a body region 16 connected to the other end of the neck. The body region 16 is connected on the other end to the handle region 18 of the hand piece. Located within the head region 12 and housed therein is the air turbine (not shown) which is in turn connected to an interchangeable dental bur 22. The bur changing mechanism is located at the socket-like openings 24 which is assessable from the rear of the head. These socket-like openings receive a bur "tool" which is used to both loosen as well as tighten the bur. The air-water spray openings 22a are located directly beneath the bur 22. It is through these openings that water is discharged from the head 12 of the hand piece propelled by air passing through the air turbine (between 20–40 psi). In the August 1992 issue of *Dentistry Today* (Vol. 11 No. 6) in an article entitled "Studies Show AIDS Virus Can Live in Hand pieces" by John Elliot, he states "Infected patient material was found in, and in some cases was coming out of, areas of equipment that were not easily cleaned or reached by chemical disinfectants." This very recent article, and others similar in findings show that the air-water spray openings 22*a* are in fact a portal for the entry of potentially harmful material.

The neck 14 region connects to form a contra-angle with the body 16 of the hand piece which then flows into the handle region 18. This handle region 18 helps to facilitate maneuverability of the instrument. The head 12, neck 14, body 16 and handle 18 all house specialized tubing through which both water and pressurized air (20–40 psi) flow through the hand piece exiting at the head region 12 through the air-water openings 22*a*. It is this pressurized air that drives the turbine located inside the head 12 of the hand piece 10. The air-water connecting hoses couple with the hand piece 10 at the opposite end of the head region 12. The connecting hoses couple in the area of the bottom opening of the hand piece 20 located at the most distal end of the handle 18. A fiber optic light source (not shown) is located adjacent to and just beneath the air-water openings 22*a*. This fiber optic light originates from a light source commonly mounted near the hand piece 10. The head 12, neck region 14, body 16, and handle region 18 house the fiber optic light tubing conducted to the head 10 providing for increased light in the oral cavity working field. A model of the hand piece described above is made available by the Midwest American (Dental) Co. and is issued under the trademark Midwest Quiet-Air Fiber Optic II.

As the above referenced article states, hand pieces of the type which are represented by FIG. 1B (reference numeral 10) may be contaminated with potentially harmful blood borne pathogens and other microbial/viral spores during normal use in the dental office setting. Areas of the hand piece 10 that are of specific concern are air-water openings 22*a*, the many grooved areas of the head 12, neck 14, body 16 and handle 18 along with the connector hose couplings located at the base of the hand piece 20. These areas both externally and internally pose as a threat to possible disease or pathogen transmission. The unfortunate spread of the HIV virus to patients in the dental office setting has prompted OSHA and the ADA (American Dental Association) to revamp the guidelines commonly used for proper dental hand piece sterilization. These new guidelines along with the above mentioned tragedies have shown us that the conventional methods of sterilization are not one hundred percent effective. The entire issue had proved to have a negative effect on the profession of Dentistry as well as increased patient anxiety.

Referring at this time to FIG. 1A and 1C, one embodiment of the hand piece cover as it functions to prevent the spread of harmful blood borne pathogens (as well as other viral/microbial spores) is designated in an "open" position. FIG. 1A (reference numeral 50) represents the right half of the hand piece cover which is specifically manufactured for use with a wide variety of conventional hand pieces. Reference numeral 28 designates the adjustable, bellowed plastic section of the head section. This is an important feature of the hand piece cover which allows for its flexibility of use with a variety of available hand pieces. This adjustable bellowed section of the head section 28 shall be constructed of a series of between 1 to 10 bands of thin plastic (measuring from between 0.5 mm to 10 mm in width and 1 to 4 cm in height). These "bands" of plastic shall be positioned vertically in a consecutive manner. This series of bands shall be connected by narrow constrictions of the same type plastic which shall be between 0.5 cm to 9.5 cm in height. This "accordion-like" bellowed section shall be rounded or otherwise contoured on both the top and bottom surfaces in order to prevent patient discomfort while the appliance is in use. FIG. 8C shows one variation of this adjustable feature 28' in which the band is located in a rear position in relation to the neck section of the bellowed section piece cover 116, corresponding to 14, as it connects to the head of the apparatus 26. Still another variation of this adjustable feature of the head section 28, is found in FIG. 8A (66–68). In this feature, a snap-on front cover 68 shall be fabricated separately and then attached to the correspondingly shaped opening formed by the plastic hinged 32–32' union of the two halves of this model (88 being the left half, 90 being the right half). The snap-on cover 68 shall be held in place by a series of between 1 to 20 raised elevations of plastic 66' (ranging from a height of 1 to 10 mm) spaced at intervals of between 0.5 to 1 mm apart. This spacing will allow a 0.5 to 1 mm extension or retraction of the snap-on cover 68 over a range of 1 to 20 mm, thereby allowing for the fit of a wide variety of conventional hand pieces.

FIG. 1A shows a version of this invention which has a "closed" back portion or rear region 26. This closed-end model will serve to eliminate the presently existing rear "exhaust" of air, water, saliva, pathogens and any other particulate matter that may happen to enter the head region of the hand piece 12 either through the air-water openings 22*a* or the bur changing openings 24 while the instrument is in use.

Other variations of the rear portion of the hand piece cover 116 are shown in FIG. 8A, 66 which designates only one addition to the closed end of 26. This feature is found in the 1 to 10 mm of curved plastic, an air deflector 54 which is attached to the top, rear portion of each half of the dental hand piece cover. The air deflector 54 shall be approximately the same width as the head section 66 of the hand piece cover (116) and shall function to deflect the air emitting from the rear openings 24 of the hand piece in a downward direction.

Other variations of the rear covering of the invention are shown in FIG. 7C, 7D and 7E. In FIG. 7C reference numeral 82 designates a rear covering 82 that has three, covered openings which allow the direct use of a changing tool. These openings shall measure between 1 to 10 mm in diameter and shall be spaced circumferentially. These openings shall be covered by a "mesh-type" filter or other such "re-sealable" material designed to for the use of the bur changing tool, but closing on withdrawal. FIG. 7D shows a similar circumferential arrangement of a series of bur tool openings. The openings of this rear cover 84 shall be covered by a "pie-shaped" arrangement of rubber or plastic material flexible enough to allow bur tool manipulation through the openings while being resilient enough in nature to return to the "closed" position once the bur tool is removed. The openings of this rear cover 84 shall be in diameter from 1 to 10 mm. The plastic or rubber portion of the rear covering 84 shall be divided into two or more divisions (three divisions shown). FIG. 7E shows a similar opening for the bur tool with the exception that rear cover 86 has an opening continuous in shape (the size and shape may vary). A similar mesh or rubber/plastic covering shall be available for rear cover 86 as well. FIG. 8A, designates the closed end rear head portion 66 of the head section of the model of the invention that includes the snap-on front covering 68. Each of the above mentioned variations are to be manufactured as a part of their respective half of the invention and are not separate attachments. The variations of the back or rear end pieces as seen in FIGS. 8B, 8C and 8*d* are separate attachments and shall be manufactured as such. FIG. 8B, shows a solid, plastic, flip-open rear cover 74. This top-hinged rear cover 74 shall be equal in diameter to the rear opening formed by the union of the two halves of the hand piece cover (88 and 90). The plastic shall be of the same thickness as each half of the hand piece cover (88 and 90) and shall be attached in such a way as to allow for the "flip-open" motion shown in FIG. 8B. The rear cover 74 shall be secured in the "closed" position by friction lock ball and socket attachment (not shown).

FIG. 8C designates still another variation of the rear covering. A solid plastic swivel-motion rear cover 76 is provided, equal in diameter to the rear opening of the hand piece cover (116), but allowing for a swivel motion upon opening and closing. This swivel motion rear cover 76 shall be of the same or similar thickness as the flip-open rear cover 74 and shall be secured by a similar "ball and socket-like" attachment to be placed at any point around the circumference of the "closed" dental hand piece cover. The swivel-motion rear cover 76 may also be secured by means of a raised elevation of plastic (or a "stop"—not shown). This "stop" shall be made of rigid plastic at a 1 to 5 mm elevation which may also occur at any point along the circumference of the rear opening on the hand piece cover.

The final of the three rear cover variations is found in FIG. 8D. In this Figure, a sliding motion rear cover 78 is shown. The sliding motion rear cover 78 is similar in size and shape to the swivel motion rear cover 76, but differs in its range of motion. Rear cover 78 may be move in a sliding direction from north to south, east to west or any straight line combinations thereof. Sliding rear cover 78 shall be held in place by a raised extension of the rear end of the head portion of the hand piece cover (116). These extensions may take the form of raised grooves or elevations which shall act as "tracks" to both guide and secure the cover 78 into the closed position. The raised elevations or "tracks" may be manufactured in the shape of "slots" placed on either side of the rear opening of the hand piece cover or may be manufactured as any shape which may cover between 1 and 50% of the rear opening of the hand piece cover, or at any such distance as may allow minimal clearance for secure closure of the cover 78.

Another very important feature of this invention is found in FIG. 1A and 1C, which shall be represented in the remaining figures as reference numeral 30. This feature is a circumferential or "pie-shaped" bur opening cover 30, which functions to guard the air-water opening 22*a*. This cover 30 shall be constructed of thin sheets of flexible rubber or plastic of a diameter ranging from 1 cm to 3 cm and shall be divided into two or more sections (a division of three equal sections is shown).

Many conventional hand pieces have as a feature a fiber optic light source used for better field illumination in the oral cavity. A thin, transparent plastic snap-in cover for the fiber optic light 56 (which shall be made available in some models) will allow for the passage of light from the fiber optic light source to the operating field. The fiber optic light source of the conventional dental hand piece is commonly placed adjacent to and immediately below the air-water openings 22*a*). The fiber optic light covering 56 may assume a wide variety of shapes (oval shape shown), and may range in size from a length and height of 1 mm to 10 mm. As an added feature, this fiber optic light cover 56 may be manufactured of a plastic or glass-like material which is magnifying in nature to even further enhance and increase the amount of light emitted by the fiber optic light source. Such magnification shall better illuminate the operating field and shall be offered as an option.

The dental hand piece cover shall be manufactured as two halves and will be held together by a series of 1 to 10 friction lock hinges (32 & 32'). The number of hinges shown in the drawings submitted may be added or subtracted as shown necessary for secure closure. The hinge (32 & 32') shall be made of rigid plastic material and shall possess a female portion 32 which shall interlock with the male portion 32'. The hinge apparatus (32,32') when in the closed position will range in size from 1 to 25 mm. Each portion of the hinge device which shall be exposed directly to the soft tissues of the oral cavity shall be contoured in shape. These hinges may be externally or internally placed at various locations along the hand piece cover.

Another feature of the hand piece cover which allows it to be used with a variety of available hand pieces is first shown in FIG. 1A. This feature, the adjustable, "bellowed plastic" section of the neck section 36, performs a similar function to the adjustable section of the head section 28. Just as the adjustable band 28 allows for the varied positioning of the head portion of the hand piece 12, this adjustable section 36, shall allow for the variations found in the contra-angles of conventional hand pieces. This contra-angle is commonly located at the junction of the head region of the hand piece 12 and the neck region of the hand piece 14 and functions to allow more ease in handling and maneuverability. The individual sections of the adjustable "bellowed plastic" section 36 shall each be horizontally arranged and will range in width from 1 to 5 cm. The height of each individual section of the adjustable section 36 shall range from 1 to 20 mm.

Conventional hand pieces of varying width will be secured inside the handpiece cover by a circumferential arrangement of "sponge-like" material. These internally placed "cushions" shall act to secure as well as to restrict the movement of the hand piece during use. The noise absorbing, hand piece stabilizing sponge material 34, shall range in size from a height of 1 mm to 20 mm, and a length of 1 mm to 20 mm and may be manufactured in a variety of shapes (rectangular shape shown). There may be at least one area of stabilizing material dispersed at various locations along the internal wall of each individual half of the hand piece cover.

Each corresponding half of the hand piece cover 116 shall have an overlapping seal as shown in FIG. 1A and 1C. This overlapping seal shall be formed by the interlocking of a male 40 and female portion 38 once the hand piece cover is locked in the "closed" position. The male portion of the overlapping seal (38 & 40) shall be composed of a raised elevation or extension of plastic ranging from a height of 1 to 10 mm and will be manufactured as a part of its respective half. The width of each elevation 40 shall range from 1 to 5 mm. The female portion 38 of the corresponding seal shall consist of two or more raised elevations of plastic and shall form a gripping aperture female portion 38, a square bottomed, angled or otherwise shaped recession that is congruent in size to the corresponding male portion 40. The male portion 40 of the overlapping seal shall also be manufactured as a part of its respective half.

FIG. 2 is a perspective view illustrating the head and neck sections of the dental hand piece cover (116) with the hand piece inserted therein. In this view the close approximation of the invention with the actual had piece itself is given to better illustrate the relationship between the fully enclosed rear cap 80 and the adjustable "bellowed plastic" portion of the head section 28 with the conventional dental hand piece.

The adjustable, sanitary, disposable dental hand piece cover 116 is designed to be used with a variety of conventional hand pieces. The hand piece cover is formed by an injection molding or thermoforming process of each half. A precision pre-formed mold constructed of metal (iron or any otherwise suitable material), may be used. A thermoplastic material transparent or opaque (which may include a variety of colors) shall be heated to the proper temperature for the injection molding process, injected anti then cooled to complete the process.

The clear and transparent or opaque plastic, hand piece cover 116 or 120, will then be removed from the mold and packaged individually. This model shall be designated Model HS-O (High-Speed without Collar).

The precision pre-formed mold shall be constructed to produce a mold thickness of 1.00 mm in all areas of the hand piece cover excluding the adjustable sections which shall have a thickness of 0.500 mm The thickness shall be same for the high-speed hand piece cover 116 utilizing the collar connector 64 (Model HS-C: High-Speed with Collar).

The hand piece cover to be used with the slow-speed dental hand piece (reference numeral 120 See FIG. 10) will also utilize the same precision pre-formed mold technique and shall be of the same thickness (1.00 mm for all sections excluding the adjustable sections which shall measure 0.500 mm in thickness). The hand piece cover 120 to utilized with the conventional slow-speed dental hand piece shall be designated Model SS-O or Model SS-C). Model SS-O shall represent the hand piece cover for slow-speed instruments that do not possess or utilize the collar connector 64a. Model SS-C shall represent the hand-piece cover for slow-speed instruments that does possess or utilize the collar connector 64a (see FIG. 10A and 10C).

The primary thicknesses listed above may range for each listed model from 0.005 mm to 7.00 mm. The thicknesses of the adjustable sections may range from 0.005 mm to 6.00 mm. The primary thicknesses of 1.00 mm and 0.500 mm are felt to be rigid enough where needed, as well as being flexible enough to perform their given tasks without fear of tearing or rupturing.

The hand piece cover 116 is injection molded and/or thermoformed to have an overall form that closely approximates that of the conventional dental hand piece 10. The hand piece cover 116 has a form that closely approximates the dental hand piece 10, FIG. 1B will also have (in general) corresponding parts as well. The dental hand piece cover 116 therefore, will include a head section corresponding to the area occupied by: adjustable band 28, 28'; a variety of rear covers 26, 74, 76, 78, 80, 82, 84, 86; head sections 50a, 50b, 50c, 66; fiber optic light cover 56; and front bur opening cover 30. The neck section of hand piece cover 116 will correspond to the area occupied by: upper hinge 32,32'; adjustable band 36 and collar connector 64. The body region of the hand piece cover 116 shall correspond to the area occupied by: lower hinge 32,32'; 62,72.

The hand piece cover 120 to be utilized with the slow-speed dental hand piece, also being manufactured by conventional injection mold methods, will also have corresponding parts to the conventional slow-speed dental hand piece. The head region of the slow-speed hand piece cover 120 shall correspond to the area occupied by: head section 92,94 and top hinge 32,32'. The neck section of hand piece cover 120 shall correspond to the area occupied by: adjustable collar 64a and connecting collar 96,98. The body/handle section shall correspond to the area occupied by: lower hinge 32,32' which shall secure the hand piece cover 120 in the slow-speed hand piece area of the handle 108 and bottom section 100,102.

The respective section (head, neck and handle) of each of the above mentioned models of the hand piece cover will define interior spaces which will communicate with each other to totally encase the head 12, neck 14, body 16 and handle 18 regions of the conventional high-speed dental hand piece 10 and the conventional slow-speed dental hand piece 118.

Figure 4:
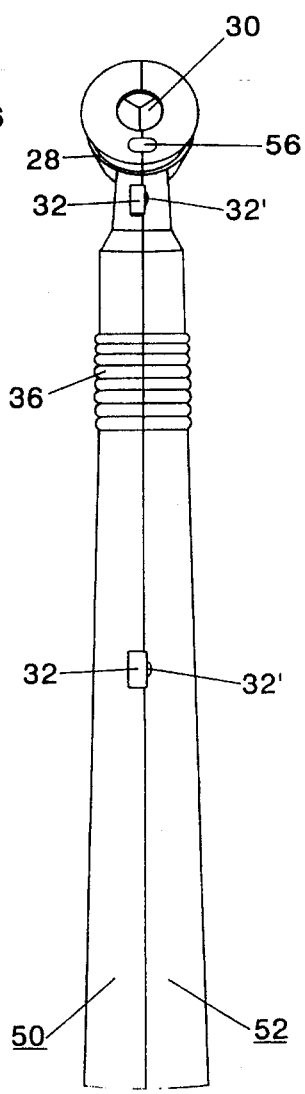
FIG. 4 is intended to show one variation of an external view of the front plan of the dental hand piece cover.
Figure 5:
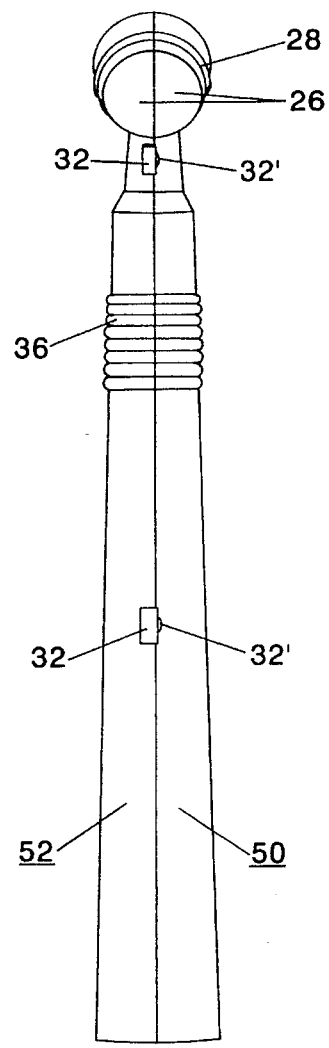
FIG. 5 is intended to show one variation of an external view of the back plan of the dental hand piece cover.

The head portion of hand piece cover 116 (used primarily for the conventional high-speed dental hand piece) shall be defined by a top, front, side and back wall which shall be identical in configuration, shape and form to the peripheral edges of adjustable section 28, front cover 30, and head section 26 (see FIGS. 3,4 and 5). This head section will have a substantially rounded and cylindrical configuration. In the model variations that include rear covers 82, 84 and 86, openings are formed to allow bur tool manipulation which shall be covered as previously described. In the model variation that includes the fiber optic light cover 56, an opening corresponding in position to the fiber optic light of the conventional dental hand piece 10 shall be formed to allow clear passage and or magnification of the fiber optic light. In model variations that include rear covers 74,76, and 78, the hand piece cover 88, 90 shall have head sections 50a, 50b, and 50c which are injection molded with a rear opening corresponding in size to covers 74, 76 and 78 (see FIGS. 8B, 8C and 8D). In the model variation that will include front snap-on cover 68, the head section 66 shall have a front opening that shall correspond in size to the interior wall of snap-on front cover 68.

The neck section of hand piece cover 116 has a substantially cylindrical configuration and an axis that extends in the straight flexed position parallel to the axis of the neck portion 14 of the conventional high-speed dental hand piece and substantially normal to the axis of the corresponding head region 12. It should be noted that the adjustable section 36 of the hand piece cover 116 will allow for forward and backward movement of the head/neck sections (at an angle range of plus or minus 45 degrees from the mid-line) in order to compensate for contra-angle variations and thereby make possible use of this device with a wide variety of available high-speed dental hand pieces.

The handle portion of hand piece cover 116 has a substantially cylindrical configuration which is elongated and tapered to correspond to the outer walls of body 16 and handle 18. In the straight flexed position, the handle region will be in direct alignment with adjustable section 36, but can also be moved or flexed both forwards and backwards at an angle range of plus or minus 45 degrees. Circumferentially arranged raised surface texture 112 with a stippling rounded dot design or raised surface texture 114 with a line pattern (or any combination of the two design patterns) are formed to better facilitate holding, handling and maneuverability while used in direct contact with the required latex or vinyl gloving.

The head section of the model of the hand piece cover 120 (to be used primarily with conventional slow-speed hand pieces; FIG. 10B) shall be defined by a top, front and side wall which shall be identical in configuration, shape, and form to the peripheral edges of head section 92, adjustable section 28, top hinge 32,32', grooved connecting portions 92', 94' and front bur opening cover 30 (see FIGS. 10A and 10C). This head portion shall have a substantially cylindrical configuration. In the model variation that included rear cover 94 the rear portion of the head section that shall correspond in size to rear cover 94.

The neck section of hand piece cover 120 has a tapered substantially cylindrical configuration and an axis that extends in the straight flexed position parallel to the axis of the neck portion 106 of the conventional slow-speed dental hand piece and substantially normal to the axis of the corresponding head region 104. It should be noted that if adjustable section 36 is used, it will allow for forward and backward movement of the head/neck sections.

This flexibility shall be in the range of plus or minus 45 degrees from the mid-line of the vertical axis to make possible use of this device with a wide variety of available slow-speed dental hand pieces.

The handle section of hand piece cover 120 has a substantially cylindrical configuration which is elongated and tapered to correspond to the outer walls of neck/body 106 and handle 108. In the straight flexed position, the handle region will be in direct alignment with adjustable section 13a or center connecting section 64a, but can be flexed or moved as the adjustable section 36 and/or center connecting section 64a will allow. Circumferential arrangement of raised surface texture 112 with a stippling (rounded) dot design or raised surface texture 114 with a line pattern (or any combination of design patterns) are formed to better facilitate holding, handling and maneuverability of the device while used in direct contact with the required latex or vinyl gloving.

The use of both clear transparent and opaque colors (as well as wide variety of designs and figures . . . for example: smiling faces, holiday symbols, cartoon characters, etc.) are designed to produce a more calm, less apprehensive, less anxious patient, be the patient child or adult. The goal of these variations are to provide for a better, more esthetic, more personable, friendly, if not even pleasant environment for the dental office setting which is often viewed as many things other than pleasant.

Operation—FIGS. 1, 7, 8, 9, 10

The manner of using the adjustable, sanitary, disposable dental hand piece cover is to be described in the paragraphs to follow for both the high-speed model and the slow-speed model.

When the need arises for use of the dental hand piece 10, the dentist will remove the dental hand piece cover 116 (or hand piece cover 120) from its protective, aseptic package and place the sterilized hand piece between the noise absorbing, stabilizing sponge material 34. Depending on the angle between the head portion 12 and the neck portion 14 of the hand piece 10, the practitioner may need to utilize the adjustable section 36 by moving the adjustable section 36 either forwards or backwards until the hand piece 10 is centered between stabilizing material 34. The head portion of the hand piece 12 (or head portion 104) is then inserted both laterally and substantially into the head portion of the hand piece cover 26 (or head portion 92) as the bur is placed through the front bur opening cover 130. Once this has been accomplished making sure that the hand piece 10 is centered between the stabilizing material 34, the hand piece cover 116 or cover 120 is then closed by aligning the female portion 32 of the hinge device directly adjacent to the male portion 32' of the hinge device and by the addition of slight force, bring the two portions of the hinge 32 and 32' together until by friction, they inter-lock. The inter-locking of the top and bottom hinges 32,32' shall also cause the two portions of the overlapping seal 38,40 and 38a, 40a to come into close proximity (thus forming the overlapping seal) which will result in the hand piece 10 becoming completely substantially encased within the hand piece cover 116 (or cover 120) as seen in FIGS. 1 and 10. As seen in FIG. 4, which represents the dental hand piece cover 116 in the "closed" position (without the bur in place), the hand piece 10 shall be totally and completely enclosed within the hand piece cover 116. Due to the pressure of the hand piece 10 against the noise absorbing, sterilizing sponge material 34 when the dental piece cover 116 is in the closed position, it is not possible for the hand piece 10 to turn or otherwise move while within the hand piece cover 116. Due to the fact that the axis of the neck portion of the hand piece cover 116 is substantially normal to the axis of the cylindrical head portion 12 and due to the bend (contra-angle) of the head 12/neck 14 portion, it will be even more improbable that the hand piece 10 will move within the cover 116. The closed rear region 26 of the hand piece cover 116 will make impossible the spraying of possible pathogens and debris filled mist from the rear openings 24 of the hand piece 10. In the model of the hand piece cover 116 utilizing rear cover 26, the bur would be changed by simply opening the device by gently forcing apart the hinge 32,32' apparatus. In models of the hand piece cover utilizing rear cover 74, the bur tool can easily and quickly be used by using the thumb to merely "flip" open the cover 74 as shown in FIG. 8B. If rear cover 76 is utilized, the bur tool can just as easily and quickly be used by using the thumb to apply an upward and outward (lateral) motion so that the rear cover 76 will open by a "swivel-like" motion. If rear cover 78 is used, the bur tool can be easily and quickly used by using the thumb (dentists') to "slide" the rear cover 78 in a downward motion in order to access the bur tool openings 24.

Of course, if rear cover 82, 84, or 86 is used the bur tool may be utilized by inserting it through the mesh or rubber coverings and into the bur tool openings 24. The flexible front bur opening cover 30 will make it virtually impossible for contaminants to reach the hand piece 10 due to the fact that the force exerted by the air-water spray will force the cover 30 open only as long as the air-water pressure is applied. Once the pressure is released, the sections of the cover will return to their closed position. In some models, the addition of sponge like material, possibly pre-soaked with an anti-viral or antibacterial solution may be placed on the back of each individual section of front cover 30 in order to provide even a greater barrier for contaminant access to the hand piece 10.

Due to the fact that the shape of the hand piece cover 116 (and cover 120) shall correspond directly and substantially to the shape of the hand piece 10 as well as the thinness of the device, the practitioner will be able to continue with desired operation of the hand piece 10 without having to make any major adjustments to normal handling and maneuvering. In addition, raised surface textures 112,114 (and a variety of combinations of both) will provide better dexterity and overall gripping of the instrument for the practitioner.

Once the desired procedure is completed, and the dentist wishes to remove the hand piece cover 116, the practitioner merely gently forces open the hinges 32,32' and effects the insertion procedure in reverse order. At this time, the hand piece cover 116 shall be properly disposed of, while the hand piece 10 will remain substantially sterile and at this time may be "cold" or chemically sterilized (as will be determined after appropriate clinical study and possible future guidelines by OSHA and the ADA).

Figures 9A, 9B, 9C:
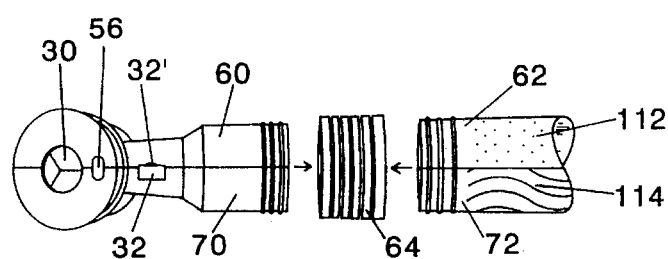
FIGS. 9A–9C to show adjustable "collar" (one variation/ model of the "bellowed plastic" adjustable band numbered 36 in the drawings).
Figure 6:
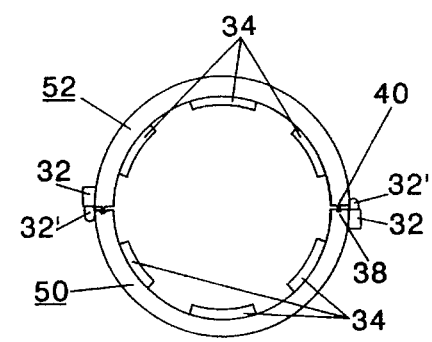
FIG. 6 is intended to show a bottom view of the dental hand piece external view of the dental hand piece cover.

The method of operation of the dental hand piece cover 116' see FIG. 9A, 9B, and 9C, which is a model variation of cover 116, is similar to the method of operation of hand piece cover 116. The major difference between the two model variations is that this hand piece cover 116' variation utilizes collar connector 64 as the adjustable section rather than adjustable section 36. Adjustable section 64 functions in a slightly different manner than section 36 as will be explained in the pages to come.

In use, when it is desired to perform a dental procedure involving the use of the high-speed dental hand piece 10 the dentist shall remove the dental hand piece cover 116' from its protective pre-packaging and insert the hand piece 10 into the aseptic and sterile hand piece cover 116'. The hand piece 10 is inserted by first placing the head section 12 of the hand piece 10 in between the top left head section 60 and the top right head section 70. Once the head portion 12 of the hand piece 10 is centered in between the two halves of the head section 60,70 of hand piece cover 116' the corresponding hinge portions 32,32' are directly aligned adjacent to each other and gentle force is then applied until the two portion of the hinge 32,32' inter-lock. At this time, care should be taken to make sure that the bur freely extends through bur opening cover 30. Collar connector 64 is at this time attached to head section 60,70 by placing either end of connector 64 immediately adjacent to the bottom connecting portion of united head section 60,70 and apply enough force to engage the first (incrementally measured) connecting portions of both the united head section 60,70 and collar connector 64. If there is any variation between the contra-angle of the hand piece 10 and the contra-angle of the hand piece cover 116', the dentist may compensate for this variation by flexing the collar connector 64 either backwards or forwards to the desired angle. Finally, left bottom section 62 and right bottom section 72 are placed around the handle portion 18 of the hand piece 10. The hinge portions 32 and 32' are aligned immediately adjacent to one another while gentle force is applied until the corresponding hinge portions 32,32' inter-lock. At this time, the bottom connecting portion of collar connector 64 is placed in direct alignment and immediately adjacent to the top connecting portion of lower handle assembly 62,72. Gentle force is then applied until the two connecting portions (incrementally are minimally measured) are engaged.

After the dental procedure is completed, the hand piece 10 withdrawn from hand piece cover 116' by applying gentle force needed to separate the hinges 32,32' and effecting the insertion procedure in reverse. Hand piece cover 116' differs from hand piece cover 116 only in the adjustable sections of the neck 14 region of the hand piece 10. The hand piece cover 116', is in all other essential respects, the same as 116.

Dental hand piece cover 120 is designed specifically for use with the slow-speed dental hand piece 118, see FIGS. 10A, 10B and 10C. In use when it is desired to use the slow-speed dental hand piece 118, the dentist shall first remove the hand piece cover 120 from its protective packaging. The dentist shall then insert the hand piece 118 into the sterile aseptic hand piece cover 120 by centering the hand piece 118 handle 108 directly in between bottom right half section 100 and bottom left half section 102. The hinges 32,32' are then directly aligned (with the corresponding hinge parts 32 and 32' being placed in direct opposition and placed immediately adjacent to one another. Gentle force is then applied until the two portions of the hinges 32,32' are caused to inter-lock. Due to the internally placed noise reducing, hand piece stabilizing sponge material 34 it is substantially impossible for the hand piece 118 to move while enclosed within. The right half of the center connecting collar 96 and the left half of the center connecting collar 98 are now placed around the neck region 106 of the hand piece 118. The hinges 32,32' of the two halves of the center connecting collar 96,98 are then aligned and placed immediately adjacent to their corresponding parts. Gentle force is then applied until the hinge portions 32,32' are caused to inter-lock. A downward force is then applied until there is minimal engagement of the top grooved portion 100', 102' of bottom section assembly 100–102 with the bottom grooved section 96", 98" of the center connecting collar assembly 96–98. At this time, the two halves of the head section 92,92 are centered around the head section of the hand piece 118. The hinge(s) 32–32' are then aligned and placed immediately adjacent to their corresponding parts. A gentle force is then applied until the hinge portions 32,32' are caused to inter-lock. Care should be taken to insure proper bur positioning through the front bur cover 30. Due to the overlapping seal 38a–40a it is highly improbable that the hand piece 118, will be contaminated with saliva, blood or other potentially harmful debris. Seeing that the shape of the hand piece cover 120 directly corresponds to that of the dental hand piece 118, the dentist will be able to retain any familiar operational techniques previously used.

The various raised textured surfaces 112 and 114 are formed to better facilitate handling and dexterity of the hand piece cover 120. If rear cover 94 is utilized with hand piece cover 120 the bur changing tool may be accessed by the practitioner using the thumb to "flip-open" the swinging rear cover 94. After the procedure has been completed, the slow-speed dental hand piece 118 is withdrawn from the cover 120 after a gentle force has been applied to separate the two portions of the hinge apparatus 32,32' by effecting the insertion procedure in reverse. There is one variation of hand piece cover 120. In models of the hand piece cover 120 that utilize an additional adjustable connecting collar 64a, the method of hand piece insertion and removal are essentially the same. The only variation is that there exists an additional collar connector 64a assembly to be joined prior to the assembling of the head section Collar connector 96, 98 is then aligned and placed immediately adjacent to center collar connector 64a. A gentle force is then applied to the receiving portions 92',94',96'98' until they minimally engage at the first graded (measured) increment. In all other essential respects, the two models are practically the same. When it is desired to remove the dental hand piece cover 120 the practitioner gently applies force sufficient enough to separate the two portions of the hinge apparatus 32,32' and effecting the insertion procedure in reverse. The used hand piece cover 120 is then properly disposed of.

Summary, Ramifications, and Scope

Accordingly, the reader will see that the adjustable, sanitary, disposable dental hand piece cover and noise reducer functions as a new and improved apparatus that can be safely, easily and conveniently used to prevent the dental hand piece from becoming a source of disease transmittal within the dental office setting. In addition, the hand piece glove and noise reducer will function to provide the dentist, patient and auxiliary personnel with a device which will reduce the harmful, potentially ear damaging noises that are constantly being produced by the dental hand piece.

The various adjustable features, as well as the different variations, allow for use of this new and improved hand piece cover with a wide variety of conventional dental hand pieces. The injection molded and/or thermoforming manufacturing process will greatly reduce production costs and thereby make the dental hand piece cover readily available as well as readily affordable. This readiness in both afford ability and availability should widespread utilization of the device and thereby afford a widespread number of patients and practitioners as well with its benefits. The individual pre-packaging will allow the hand piece cover to remain sterile during shipment and will also keep it free from accidental contamination in the dental office setting prior to patient use. Furthermore, the adjustable, sanitary, disposable dental hand piece cover and noise reducer has the additional advantages in that:

it will provide the practitioner with a new and improved hand piece cover that a possesses a superior barrier that prevents leakage and contamination.

It provides for the elimination of potentially harmful rear hand piece emissions.

It provides the practitioner with a hand piece cover that can be used with the conventional slow-speed hand piece.

It provides a superior method of stabilization of the hand piece within the hand piece cover.

It provides the practitioner with a hand piece cover which allows for the unobstructed use of the fiber optic light during the dental procedure.

It provides the practitioner with a hand piece cover which allows for the magnification of conventional fiber optic light.

It permits the dentist to access the rear of the hand piece without exposing the hand piece to the contaminants of the oral cavity.

It provides the practitioner with a disposable, sanitary hand piece cover that is functionally adjustable.

It provides a superior and more secure method of hand piece closure, by use of the friction-lock hinge apparatus.

It permits the practitioner to now color coordinate the hand piece with the office decor thereby increasing office esthetics.

It provides the profession with a device which by its (colorful and/or designed) appearance will help alleviate and/or reduce patient anxiety directed towards the hand piece sound or appearance.

It provides a new and improved hand piece cover superior in ease of use and manipulation.

It permits more wide spread use and ease of afford ability, by its manufacturing process.

Although the description above contains many specificity's, these should not be construed as limiting the scope of the invention but as merely providing illustrations of the presently preferred embodiments of this invention. For example, the hand piece cover may have other shapes, such as, substantially elongated, oval, trapezoidal or rectangular as well as cylindrical. The adjustable sections may take on these same shapes as well, and the over lapping closure seal may be extended or reduced.

Thus the scope of the invention should be determined by the new and appended claims and their legal equivalents, rather than only by the examples given.

What is claimed is:

1. A sanitary, disposable cover for a dental handpiece, said cover comprising;

(a) a flexible, substantially cylindrically shaped upper head section for receiving the head portion of a dental handpiece, said head section including means for adjusting the size of said head section for accommodating different sized handpieces;

(b) a central, substantially cylindrically shaped adjustable neck section for receiving the neck portion of a dental handpiece, said neck section having two ends, one of said ends being joined to said head section, said neck section further including means for adjusting the angular position of said neck section to accommodate different handpiece angulations;

(c) a rigid, substantially cylindrically shaped lower body section for receiving the handle portion of a dental handpiece, said lower body section being joined to the other of said ends of said neck section;

wherein said cover includes first and second half portions, each said half portion including a pair of edge regions extending longitudinally therealong, each said edge region of each half portion including interlocking means therealong which mates with a corresponding interlocking means of each edge region of the other of said half portions, said interlocking means and said edge regions form an interlocking closure seal, adapted to be engaged and disengaged so that a handpiece may be inserted or removed from said cover.

2. A cover for a dental handpiece as recited in claim 1, wherein the axis of the head section extends at an angle to the axis of the neck section.

3. A cover for a dental handpiece as recited in claim 1, wherein said head section includes front and rear walls, said front wall including at least one opening for allowing passage of a bur therethrough.

4. A cover for a dental handpiece as recited in claim 3, wherein said front wall is removable.

5. A cover for a dental handpiece as recited in claim 3, further comprising at least one additional opening in said front wall.

6. A cover for a dental handpiece as recited in claim 3, wherein said rear wall is removable.

7. A cover for a dental handpiece as recited in claim 3, wherein said rear wall is hingedly attached to said head section.

8. A cover for a dental handpiece as recited in claim 1, wherein at least one of said interlocking means comprises a raised elevation.

9. A cover for a dental handpiece as recited in claim 8, wherein at least one of said interlocking means comprises a groove for receiving said at least one raised elevation via friction interlock.

10. A cover for a dental handpiece as recited in claim 1, further including means for reducing noise of a dental handpiece, said reducing means located within the interior of said cover.

11. A cover for a dental handpiece as recited in claim 1, further including at least one hinge for hingedly attaching said half portions together.

12. A cover for a dental handpiece as recited in claim 1, wherein said neck section further includes an adjustable collar portion.

13. A cover for a dental handpiece as recited in claim 1, wherein said means for adjusting the size of said head section comprises a bellowed section.

14. A cover for a dental handpiece as recited in claim 1, wherein said means for adjusting the angular position of said neck section comprises a bellowed section.

* * * * *